US012649044B2

(12) United States Patent
Murray et al.

(10) Patent No.: US 12,649,044 B2
(45) Date of Patent: Jun. 9, 2026

(54) REUSABLE URINARY CATHETER KITS

(71) Applicant: Hollister Incorporated, Libertyville, IL (US)

(72) Inventors: Michael G. Murray, Ballina (IE); Horacio Montes De Oca, Ballina (IE); Gary W. Inglese, Deerfield, IL (US); Rebecca M. Leece, Bicester (GB); Sean McNulty, Dublin (IE); Jerome A. Henry, Castlebar (IE); Dean W. Hacker, Ballinrobe (IE); Padraig M. O'Flynn, Ballina (IE); Martin McMenamin, Lifford (IE); David J. Farrell, Ballina (IE); Paul O'Malley, Hollymount (IE)

(73) Assignee: Hollister Incorporated, Libertyville, IL (US)

( * ) Notice: Subject to any disclaimer, the term of this patent is extended or adjusted under 35 U.S.C. 154(b) by 1177 days.

(21) Appl. No.: 17/616,617

(22) PCT Filed: Jun. 10, 2020

(86) PCT No.: PCT/US2020/037011
§ 371 (c)(1),
(2) Date: Dec. 3, 2021

(87) PCT Pub. No.: WO2020/252032
PCT Pub. Date: Dec. 17, 2020

(65) Prior Publication Data
US 2022/0226603 A1 Jul. 21, 2022

Related U.S. Application Data

(60) Provisional application No. 62/861,066, filed on Jun. 13, 2019.

(51) Int. Cl.
A61M 25/00 (2006.01)
A61L 2/18 (2006.01)
A61L 103/15 (2026.01)

(52) U.S. Cl.
CPC ............. A61M 25/002 (2013.01); A61L 2/18 (2013.01); *A61L 2103/15* (2026.01); *A61M 2025/0019* (2013.01)

(58) Field of Classification Search
CPC ........... A61M 25/002; A61M 25/0017; A61M 25/0019; A61L 2/18; A61L 2202/24
See application file for complete search history.

(56) References Cited

U.S. PATENT DOCUMENTS 1,120,549 A 12/1914 Schellberg
3,794,042 A 2/1974 De Klotz et al.
(Continued)

FOREIGN PATENT DOCUMENTS

DE 3819257 C1 7/1989
DE 10334372 A1 2/2005
(Continued)

OTHER PUBLICATIONS

International Search Report and Written Opinion Dated Nov. 13, 2020 for International Application No. PCT/US2020/037011.

*Primary Examiner* — Regina M Yoo
(74) *Attorney, Agent, or Firm* — Cook Alex Ltd.

(57) ABSTRACT

Kits are provided for storing, transporting, and sterilizing reusable urinary catheters. A reusable urinary catheter stored within a housing of the kit may be sterilized between uses using a sterilization fluid or sterilizing light. If the reusable urinary catheter is sterilized using a sterilization fluid, the housing may include a manually actuated or electromechanical pump to circulate the sterilization fluid through the housing. The reusable urinary catheter may include a funnel secured to a catheter shaft, with a plurality of lateral open- (Continued)

ings defined in the funnel, which provide fluid communication between an interior of the funnel and an external surface of the catheter shaft. By allowing fluid communication between the interior of the funnel and the external surface of the catheter shaft, the lateral openings allow for fluid sterilization of both internal and external surfaces of the catheter shaft.

15 Claims, 13 Drawing Sheets

(56) References Cited

U.S. PATENT DOCUMENTS

| | | | |
|---|---|---|---|
| 3,956,011 | A | 5/1976 | Carleton |
| 4,170,996 | A | 10/1979 | Wu |
| 4,754,877 | A | 7/1988 | Johansson et al. |
| 5,226,530 | A | 7/1993 | Golden |
| 6,695,831 | B1 | 2/2004 | Tsukada et al. |
| 7,537,589 | B2 | 5/2009 | Tsukada et al. |
| 8,933,416 | B2 | 1/2015 | Arcand et al. |
| 2003/0017073 | A1 | 1/2003 | Eckhardt et al. |
| 2006/0025753 | A1 | 2/2006 | Kubalak et al. |
| 2007/0066963 | A1 | 3/2007 | Tanghoj |
| 2008/0091145 | A1 | 4/2008 | House |
| 2008/0200907 | A1 | 8/2008 | Nestenborg |

| | | | |
|---|---|---|---|
| 2009/0071851 | A1 | 3/2009 | Maki et al. |
| 2009/0101531 | A1 | 4/2009 | Nordholm et al. |
| 2009/0299334 | A1 | 12/2009 | Nishtala et al. |
| 2010/0072399 | A1* | 3/2010 | Street .......................... A61L 2/10 |
| | | | 250/492.1 |
| 2011/0114520 | A1 | 5/2011 | Matthison-Hansen |
| 2011/0137296 | A1 | 6/2011 | Tanghoj |
| 2012/0168324 | A1 | 7/2012 | Carleo |
| 2012/0316515 | A1 | 12/2012 | Terry |
| 2013/0267888 | A1 | 10/2013 | Rhodes et al. |
| 2014/0264074 | A1 | 9/2014 | Victor et al. |
| 2016/0136391 | A1 | 5/2016 | Foley |
| 2018/0169377 | A1 | 6/2018 | Hickmott et al. |
| 2018/0338475 | A1 | 11/2018 | Ala'Aldeen et al. |

FOREIGN PATENT DOCUMENTS

| | | | | | |
|---|---|---|---|---|---|
| DE | 102004013712 | B3 | 8/2005 | | |
| DE | 102007021118 | A1 | 11/2008 | | |
| JP | 2011139881 | A | 7/2011 | | |
| JP | 2011139882 | A | 7/2011 | | |
| WO | 2005092418 | A1 | 10/2005 | | |
| WO | 2005092419 | A1 | 10/2005 | | |
| WO | 2015075841 | A1 | 5/2015 | | |
| WO | 2015089189 | A2 | 6/2015 | | |
| WO | 2015184365 | A1 | 12/2015 | | |
| WO | WO-2016206701 | A1 * | 12/2016 | .......... | A61M 25/001 |
| WO | WO-2020223043 | A1 * | 11/2020 | ............ | A61L 2/085 |

* cited by examiner

REUSABLE URINARY CATHETER KITS

CROSS-REFERENCE TO RELATED APPLICATION

This application is a National Stage Entry of International Application No. PCT/US2020/037011, filed Jun. 10, 2020, which claims the benefit of U.S. Provisional Application Ser. No. 62/861,066, filed Jun. 13, 2019, all of which are hereby incorporated by reference in their entirety.

BACKGROUND

Field of the Disclosure

The present disclosure generally relates to urinary catheters. More particularly, the present disclosure relates to reusable urinary catheter kits.

Description of Related Art

Catheters are used to treat many different types of medical conditions and typically include an elongated shaft that is inserted into and through a passageway or lumen of the body. Catheters, and in particular intermittent catheters, are commonly used by those who suffer from various abnormalities of the urinary system, such as urinary retention or incontinence. With the advent of intermittent catheters, individuals with urinary system abnormalities can self-insert and self-remove intermittent catheters several times a day.

Urinary catheters are frequently provided as disposable, single-use items. A user will remove the catheter from a package, use the catheter once, and then dispose of the catheter and the package. Reusable urinary catheters could, thus, be advantageous in reducing the amount of waste created by the use disposable catheters, but there are various challenges associated with the use of reusable catheters (including storage, transport, and sterilization) that must be overcome before widespread acceptance and use of reusable catheters.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a reusable urinary catheter kit includes a housing and a reusable urinary catheter. The housing includes a first member, a second member defining a lid, a tether extending between the first and second members, and a chamber defined by the first and second members and the tether, with the first member defining an access opening of the chamber. The reusable urinary catheter is at least partially positioned within the chamber. The second member is adjustably associated to the first member by the tether and configured to move between a closed condition in which the lid overlays the access opening to enclose the reusable urinary catheter within the chamber and an open condition in which the lid is spaced from the access opening.

In another aspect, a method for sterilizing a reusable urinary catheter includes positioning a reusable urinary catheter within a chamber of a housing. The housing includes a first member, a second member defining a lid, and a tether extending between the first and second members, with the chamber being defined by the first and second members and the tether, and with the first member defining an access opening of the chamber. The second member is moved from an open condition in which the lid is spaced from the access opening to a closed condition in which the lid overlays the access opening to enclose the reusable urinary catheter within the chamber, followed by sterilization of the reusable urinary catheter within the chamber.

In yet another aspect, a reusable urinary catheter kit includes a housing, a chassis removably positioned within the housing, and a reusable urinary catheter removably secured to the chassis. The housing includes a base having first and second ends, with a lid pivotally secured to the first end of the base, movable between a closed condition overlaying the base and an open condition pivoted away from the base, and defining an aperture. The housing further includes a cap pivotally secured to the second end of the base and movable between a closed condition overlaying the aperture and an open condition pivoted away from the base and the lid. The chassis defines a fluid flow path extending between an access opening and the reusable urinary catheter, with the access opening being generally aligned with the aperture when the chassis is positioned within the base and the lid is in the closed condition.

In another aspect, a method for sterilizing a reusable urinary catheter includes securing a reusable urinary catheter to a chassis and positioning the chassis into a housing having a base, a lid pivotally secured to a first end of the base, and a cap pivotally secured to a second end of the base. The lid is moved from an open condition pivoted away from the base to a closed condition overlaying the base. The cap is moved from an open condition pivoted away from the base and the lid to a closed condition overlaying an aperture defined by the lid. The reusable urinary catheter is then sterilized within the housing.

In yet another aspect, a urinary catheter includes a catheter shaft and a funnel secured to the catheter shaft, with proximal and distal openings and a plurality of lateral openings defined in the funnel.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figure 1:
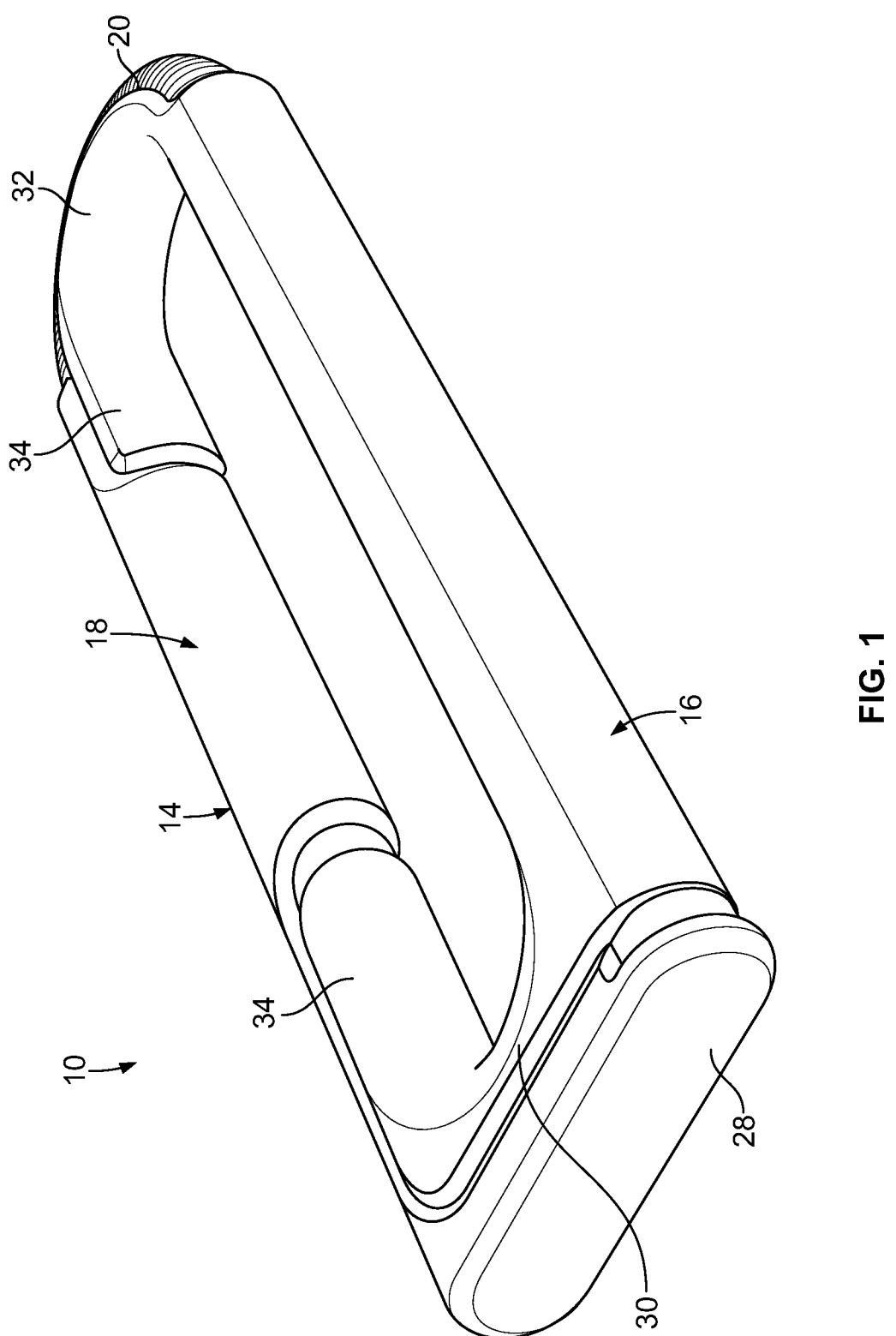
FIG. 1 is a perspective view of a reusable urinary catheter kit according to an aspect of the present disclosure, with a housing of the kit in a closed condition prior to use.
Figure 9:
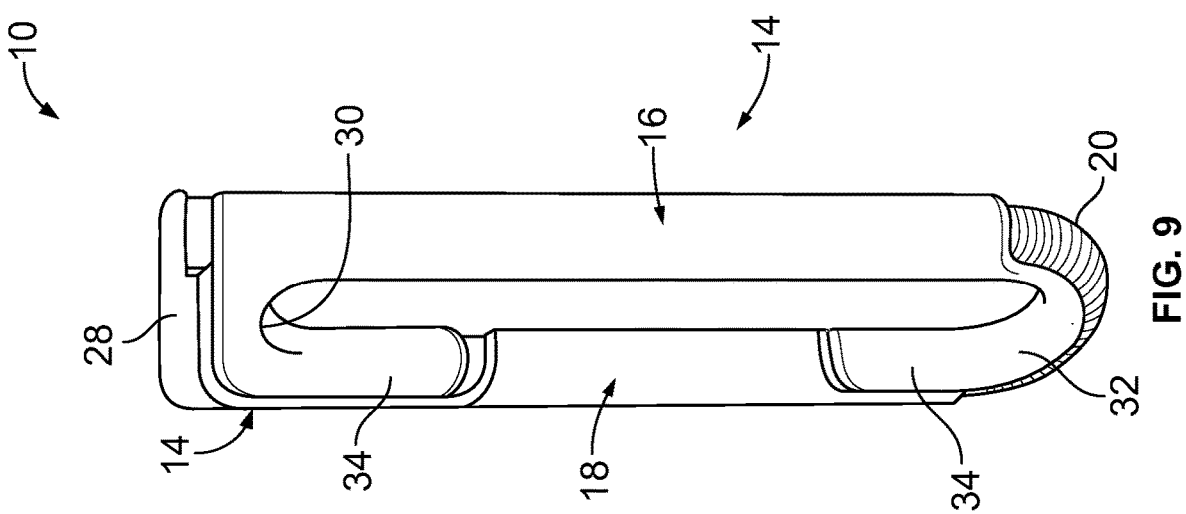
FIG. 9 is a perspective view of the kit of FIG. 1, in a closed condition following use.
Figure 8:
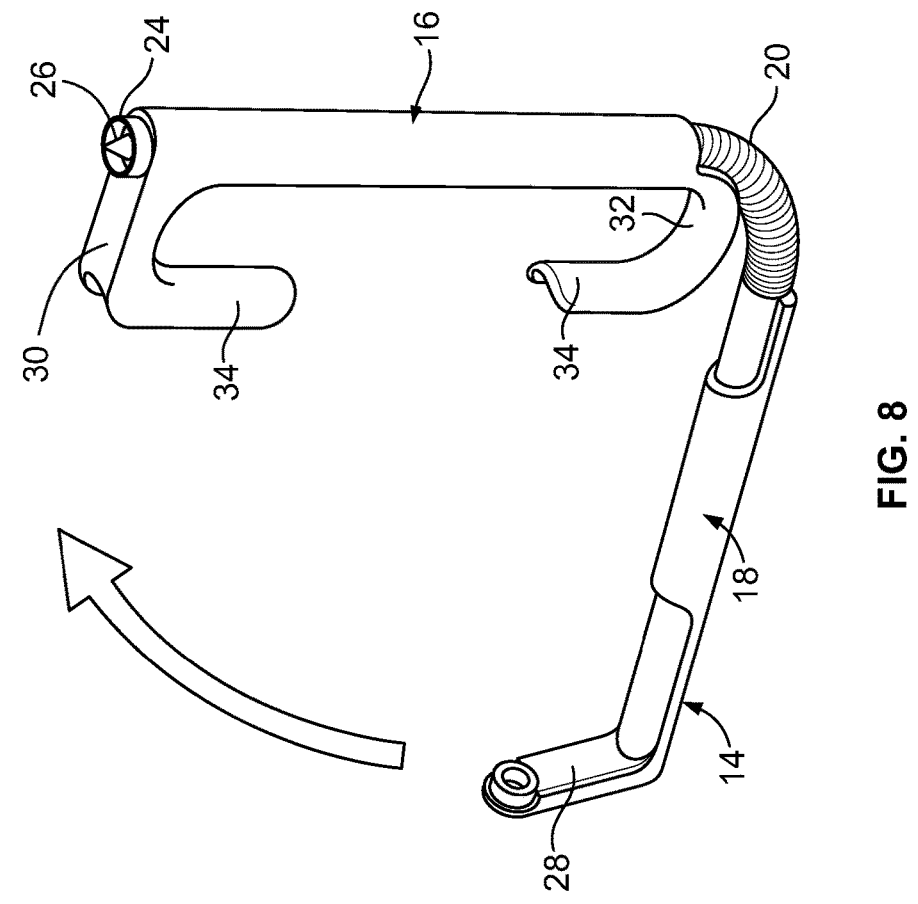
FIG. 8 is a perspective view of the kit of FIG. 1, with the housing being moved from the open condition of FIG. 7 toward a closed condition.

Reusable urinary catheter kits according to the present disclosure and their individual components may be variously configured without departing from the scope of the present disclosure, but in one embodiment, a reusable urinary catheter kit 10 is configured as shown in FIG. 1, with FIGS. 2-9 showing steps of using and then sterilizing a reusable urinary catheter 12 (FIGS. 5 and 6) of the kit 10. In particular, the illustrated kit 10 includes a housing or body 14 having first and second members 16 and 18 joined by a tether 20. The first and second members 16 and 18 may be formed of a generally rigid material (e.g., a plastic material), while the tether 20 may be formed of a flexible and/or deformable material (e.g., an elastomeric material). By such a configuration, the tether 20 allows the position of the second member 18 to be adjusted with respect to the first member 16. For example, FIGS. 1 and 9 show the second member 18 in a closed condition, while FIGS. 2-8 show the second member 18 in various open conditions. The closed and open conditions will be described in greater detail herein.

Figure 7:
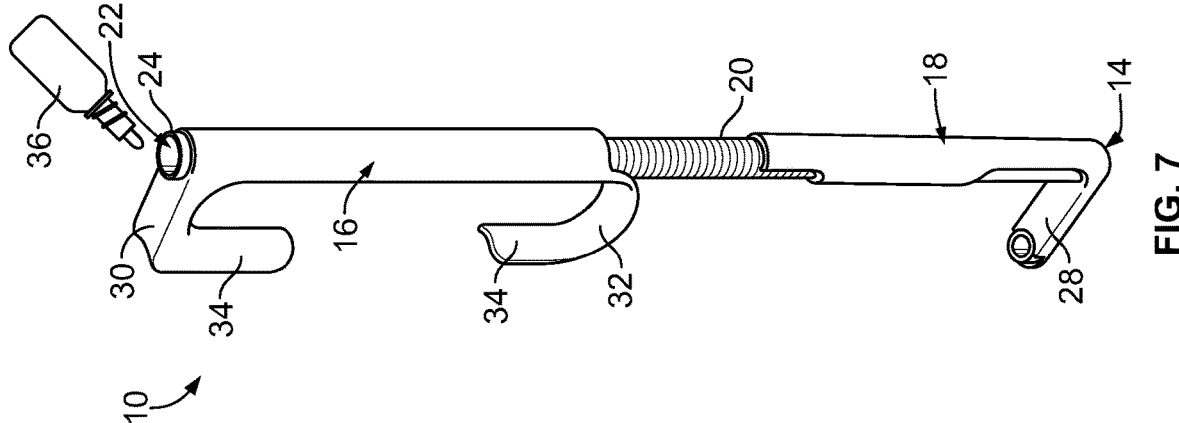
FIG. 7 is a perspective view of the kit of FIG. 1, with the housing being at least partially filled with a sterilization fluid.
Figure 6:
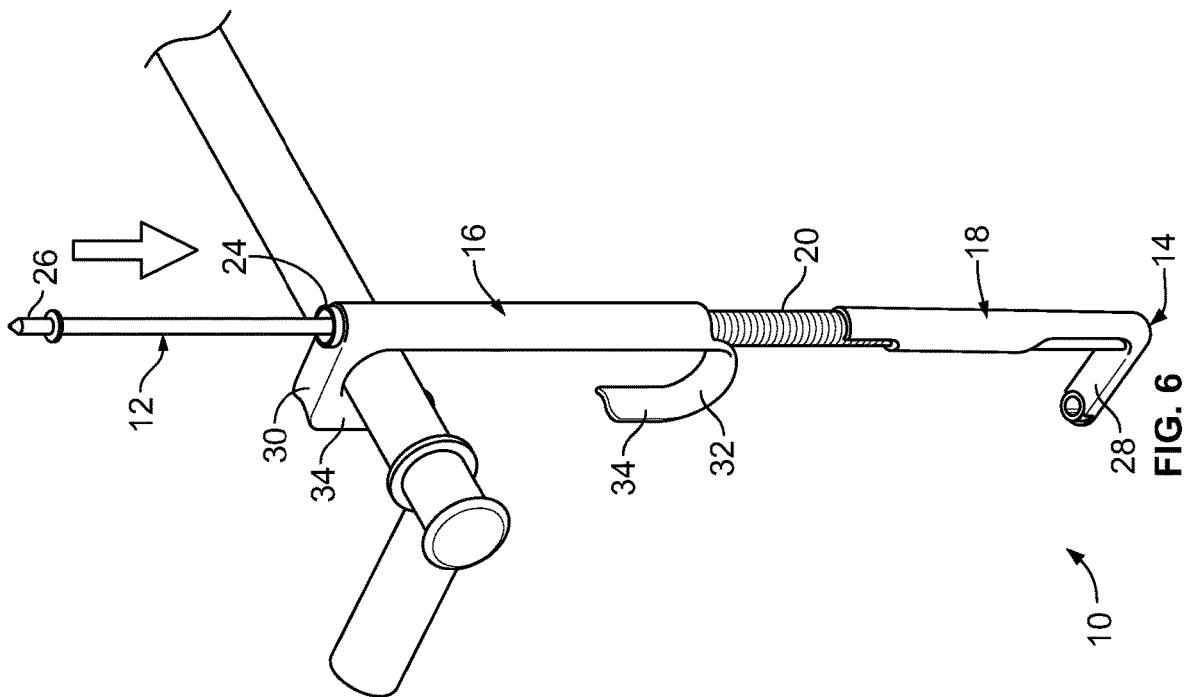

The first and second member 16 and 18 and the tether 20 each include or define a hollow section, with the hollow section of the tether 20 communicating with the hollow sections of the first and second members 16 and 18 to collectively define a single open region referred to herein as a chamber 22 (FIG. 7). The chamber 22 is sized and configured to receive the reusable urinary catheter 12, with a distal portion of the reusable urinary catheter 12 positioned in the hollow section of the second member 18, a midsection of the reusable urinary catheter 12 positioned in the hollow section of the tether 20, and a proximal portion of the reusable urinary catheter 12 positioned in the hollow section of the first member 16. In the illustrated embodiment, the first member 16 defines an access opening 24 of the chamber 22 (FIGS. 2-8) by which the reusable urinary catheter 12 may be removed from and returned to the chamber 22. The reusable urinary catheter 12 may be entirely received within the chamber 22 or a portion of the reusable urinary catheter 12 (e.g., all or a portion of an introducer tip 26 associated with a proximal end of the reusable urinary catheter 12) may extend through the access opening 24 and remain outside of the chamber 22 (as in FIGS. 2-4), which may assist in removing the reusable urinary catheter 12 from the chamber 22.

In the closed condition of FIG. 1, a lid 28 of the second member 18 overlays the access opening 24 to enclose the reusable urinary catheter 12 within the chamber 22. The lid 28 preferably forms a fluid-tight seal with the access opening 24 for fluid sterilization of the reusable urinary catheter 12 within the chamber 22, as will be described in greater detail herein. The housing 14 is in the closed condition of FIG. 1 during storage and transportation of the reusable urinary catheter 12. It will be seen that the housing 14 is essentially folded in half onto itself in the closed condition (compare FIGS. 1 and 4), with the hollow sections of the first and second members 16 and 18 being substantially parallel to each other (instead of being coaxial, as in FIG. 4), thus decreasing the length of the kit 10 and making it more portable. As can also be seen in FIG. 1, the housing 14 defines a closed loop in the closed condition, which accommodate a user's fingers for improved handling and transport.

Figures 2, 3:
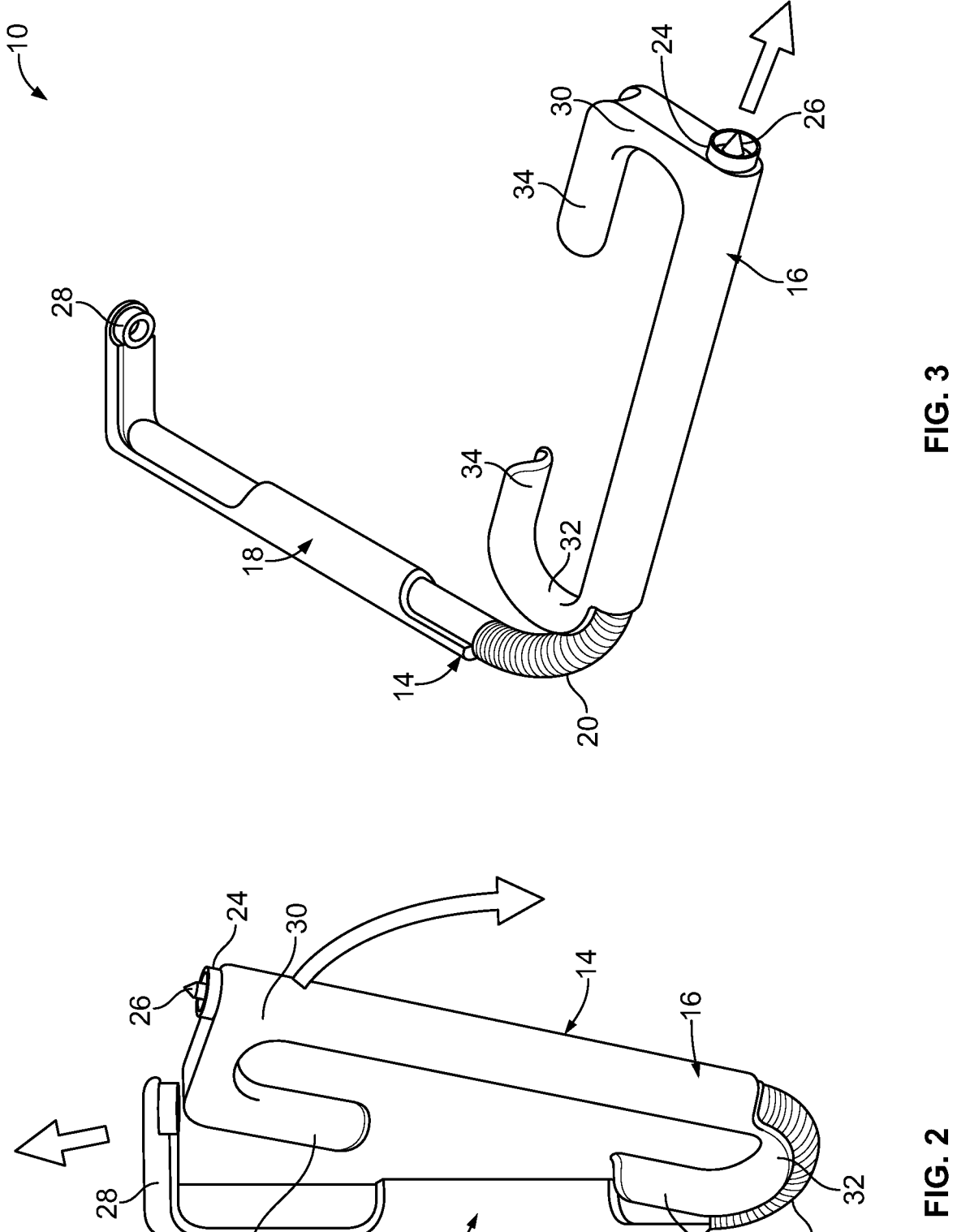
FIGS. 2-4 are perspective views of the kit of FIG. 1, with the housing in various open conditions.
Figure 4:
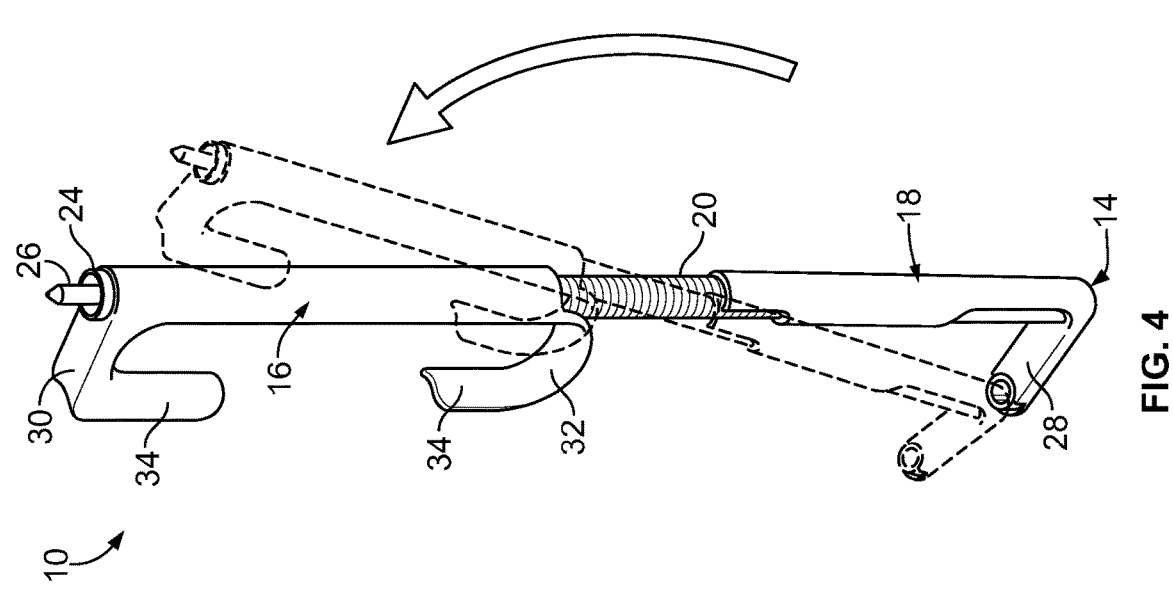

Due to the flexibility and/or deformability of the tether 20, the position of the second member 18 with respect to the first member 16 may be adjusted (e.g., by pivoting the first and second members 16 and 18 away from each other) to move the lid 28 away from the access opening 24 to allow access to the chamber 22 (including the reusable urinary catheter 12, if positioned therein) via the access opening 24. Thus, FIGS. 2-4 show the second member 18 being continuously moved or pivoted away from the first member 16 from the substantially parallel, closed condition of FIG. 1 to the open, generally coaxial condition of FIG. 4. If the reusable urinary catheter 12 has previously been used and there is a sterilization fluid in the chamber 22, the sterilization fluid may be poured out of the chamber 22 via the access opening 24, as in FIG. 3.

Figure 5:
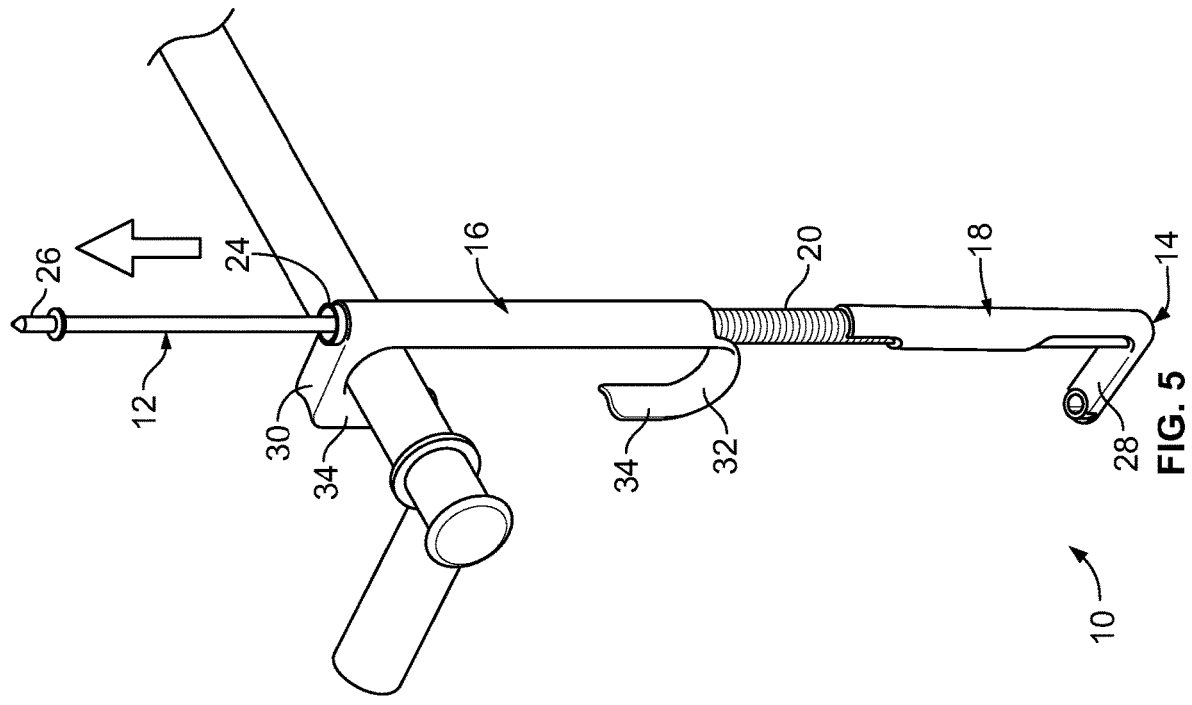
FIGS. 5 and 6 are perspective views of the kit of FIG. 1, with the housing in an open condition and suspended from a support, with a reusable urinary catheter being removed from the housing in FIG. 5 and returned to the housing in FIG. 6.

When the housing 14 has been moved to the elongated, generally coaxial configuration of FIG. 4 (referred to herein as a fully open condition), it may be hung from or otherwise supported by a handrail, toilet paper holder, towel rail, sink lip, or other support, with the access opening 24 oriented upwardly (FIG. 5). To that end, the first member 16 may be provided with a proximal arcuate extension 30 that is associated with and extends away from a proximal portion of the first member 16. The proximal arcuate extension 30 is shown as defining an approximately 180° arc, but it may be differently configured (or omitted) without departing from the scope of the present disclosure.

The first member 16 is shown as also having a distal arcuate extension 32 that is associated with and extends away from a distal portion of the first member 16. The distal arcuate extension 32 is shown as being substantially a mirror image of the proximal arcuate extension 30 and extending away from the first member 16 in the same direction as the proximal arcuate extension 30. Such a configuration may be advantageous by providing the tether 20 with a guide or support, with the tether 20 being laid along a portion of the distal arcuate extension 32 when moving the second member 18 from the open condition to the closed condition. In the illustrated embodiment, each arcuate extension 30, 32 includes a free end 34, with the free ends 34 of the arcuate extensions 30 and 32 being positioned directly adjacent to the second member 18 when the second member 18 is in the closed condition of FIG. 1. Each free end 34 preferably has a shape that is complementary to the shape of the portion of the second member 18 brought into the vicinity of the free end 34 in the closed condition of FIG. 1. For example, the free ends 34 are shown as each defining an arcuate channel facing and receiving an associated cylindrical portion of the second member 18, though it should be understood that the free ends 34 may be differently configured without departing from the scope of the present disclosure.

With the housing 14 suspended from a suitable support (or held by hand or laid on a horizontal surface), the reusable urinary catheter 12 may be removed from the chamber 22 via the access opening 24, as in FIG. 5. The user uses the reusable urinary catheter 12 for catheterization and then returns the reusable urinary catheter 12 to the chamber 22, as in FIG. 6.

Depending on the selected approach to sterilization of the reusable urinary catheter 12, the housing 14 may either be returned to its closed condition (as in FIGS. 8-9) or temporarily remain in the open condition. For example, if the reusable urinary catheter 12 is to be sterilized using a sterilization fluid 36, as in FIG. 7, the housing 14 remains open to allow the chamber 22 to be partially filled with a sterilization fluid 36 via the access opening 24. With the sterilization fluid 36 in the chamber 22, the housing 14 may be returned to the closed condition (as in FIGS. 8-9) to seal the reusable urinary catheter 12 and sterilization fluid 36 within the chamber 22. The sterilization fluid 36 may be circulated through the chamber 22 to sterilize the reusable urinary catheter 12 before the next use, with the sterilization fluid 36 being emptied from the chamber 22 (as in FIG. 3) prior to use. The sterilization fluid may be any suitable sterilization fluid, and when the catheter is a hydrophilic catheter, the sterilization fluid also may serve as a hydration medium that hydrates the hydrophilic material of the catheter.

The manner in which the sterilization fluid 36 is circulated through the chamber 22 may vary without departing from the scope of the present disclosure. For example, the housing 14 may be manually agitated (e.g, by shaking it) to circulate the sterilization fluid 36 through the chamber 22. Alternatively, the kit may be provided with a pump in fluid communication with the chamber, as in the embodiments of FIGS. 10-13.

Figures 10, 11:
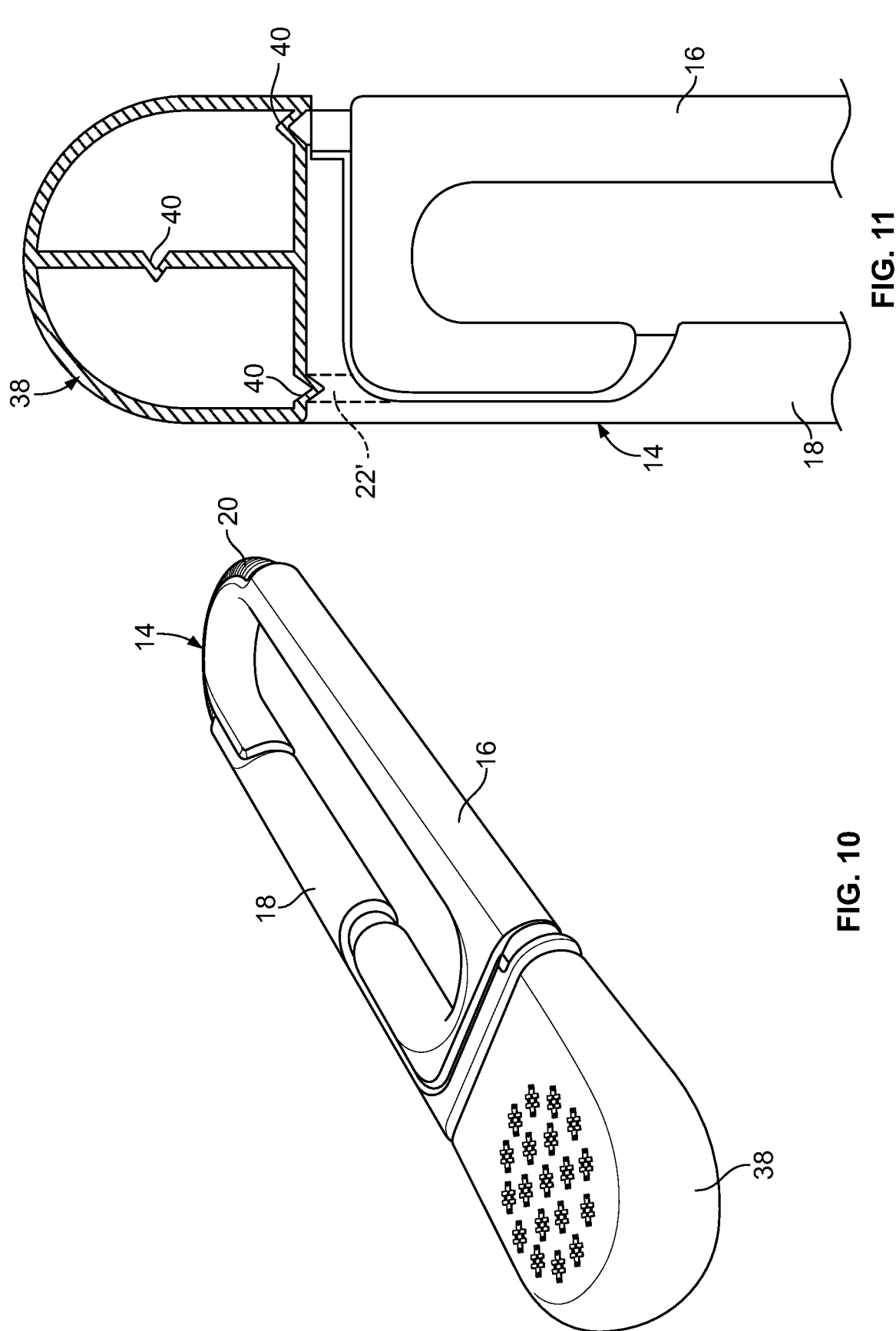
FIG. 10 is an alternative embodiment of the kit of FIG. 1, with a housing of the kit in a closed condition.
FIG. 11 is a cross-sectional view of the housing of FIG. 10.

In the embodiment of FIGS. 10 and 11, a pump is incorporated into the second member, with the chamber being extended to communicate with the pump. In FIGS. 10 and 11, the pump 38 is configured to be manually actuated, with a user squeezing or otherwise manipulating the pump 38 to circulate sterilization fluid 36 through the extended chamber 22' (which may define a loop). For example, the pump 38 may be configured as a bulb to alternately draw sterilization fluid 36 into and then expel sterilization fluid 36 from the pump 38. A manually actuated pump 38 may also include one or more one-way valves 40 (FIG. 11), which enforces circulation of the sterilization fluid 36 through the pump 38 (and, hence, through the chamber 22') in only one direction.

Figures 12, 13:
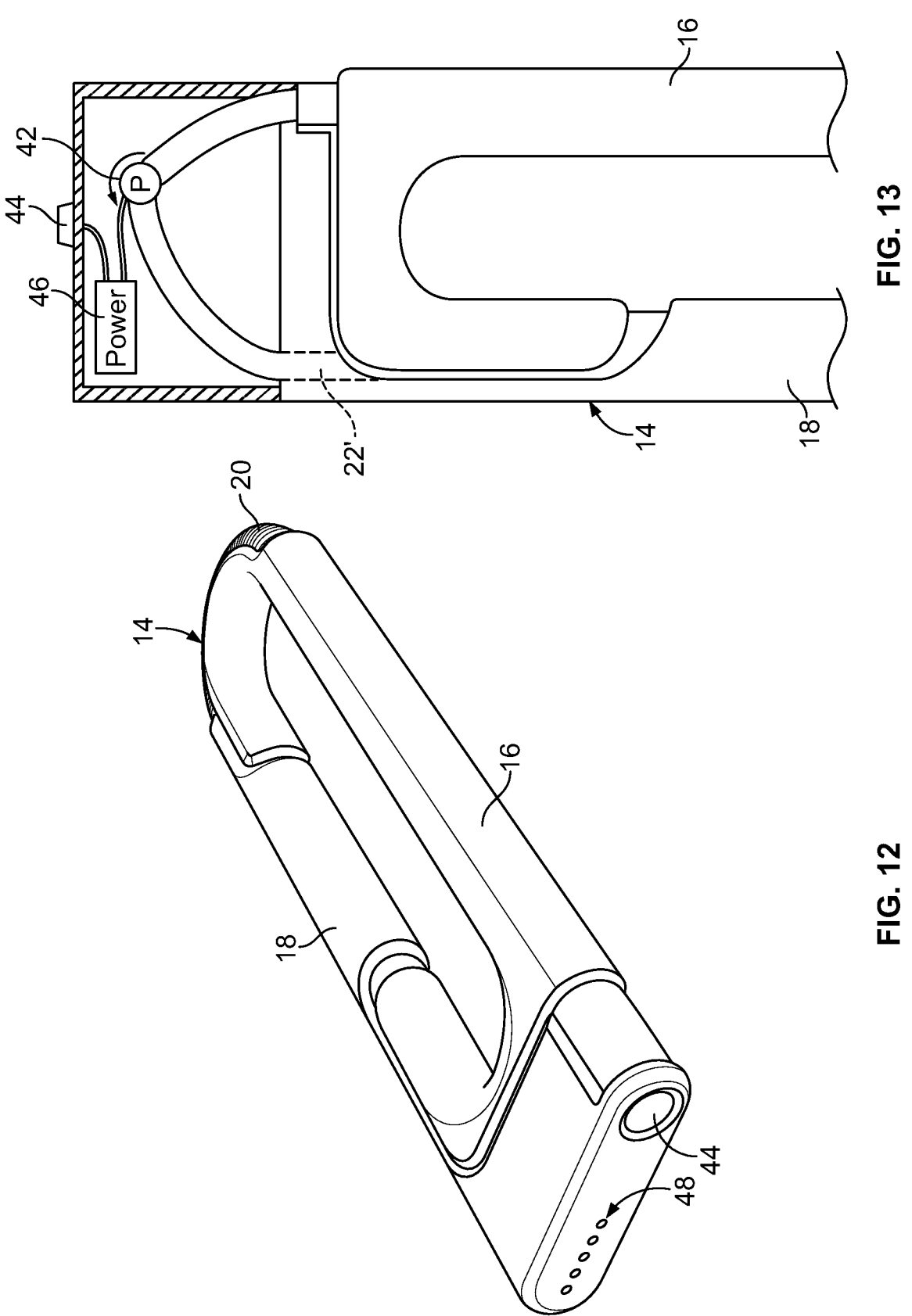
FIG. 12 is a perspective view of an alternative embodiment of the kit of FIG. 1, with a housing of the kit in a closed condition.
FIG. 13 is a cross-sectional view of the housing of FIG. 12.
Figure 14:
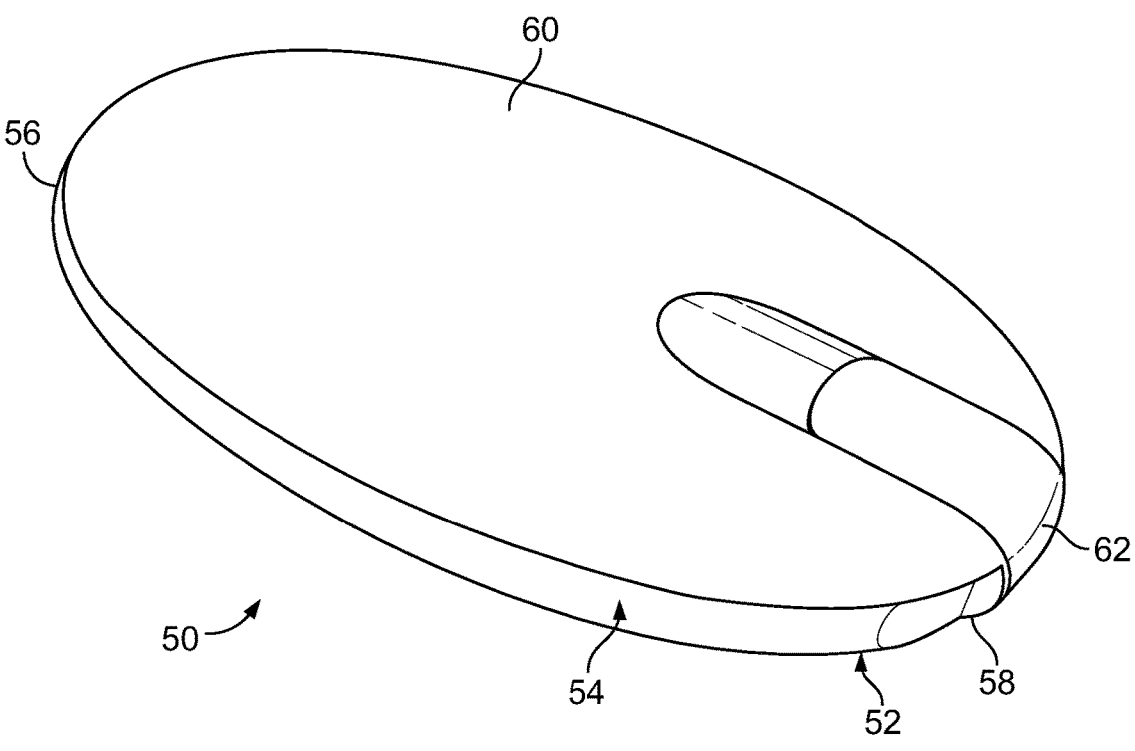
FIG. 14 is a perspective view of another embodiment of a reusable urinary catheter kit according to an aspect of the present disclosure, with a housing of the kit in a closed condition.

In the embodiment of FIGS. 12 and 13, an electromechanical pump 42 is provided for circulating sterilization fluid through an extended chamber 22' (which may define a loop). The housing 14 may be provided with a button or actuator 44 or the like for actuating a power source 46 of the pump 42, along with indicators 48 (e.g., LEDs) showing the status of the sterilization process. In addition to visual indicators, an audible indicator (e.g., an alarm) may be provided to signify that the reusable urinary catheter 12 has been suitably sterilized and is ready for reuse.

Alternatively, or in addition to the use of a sterilization fluid, a sterilizing light may be employed to sterilize the reusable urinary catheter 12. In such an embodiment, the reusable urinary catheter 12 may be enclosed within the chamber 22 following use without adding a sterilization fluid 36. With the housing 14 in the closed condition of FIG. 9, at least one light source associated with the chamber 22 is activated by the user (e.g., by pressing a button), causing the at least one light source to irradiate at least a portion of the reusable urinary catheter 12 with sterilizing light (e.g., ultraviolet light). As in the embodiment of FIGS. 12 and 13, the housing 14 of such a kit may be provided with one or more indicators 48 (visible and/or audible) displaying the status of the sterilization process.

Figure 15:
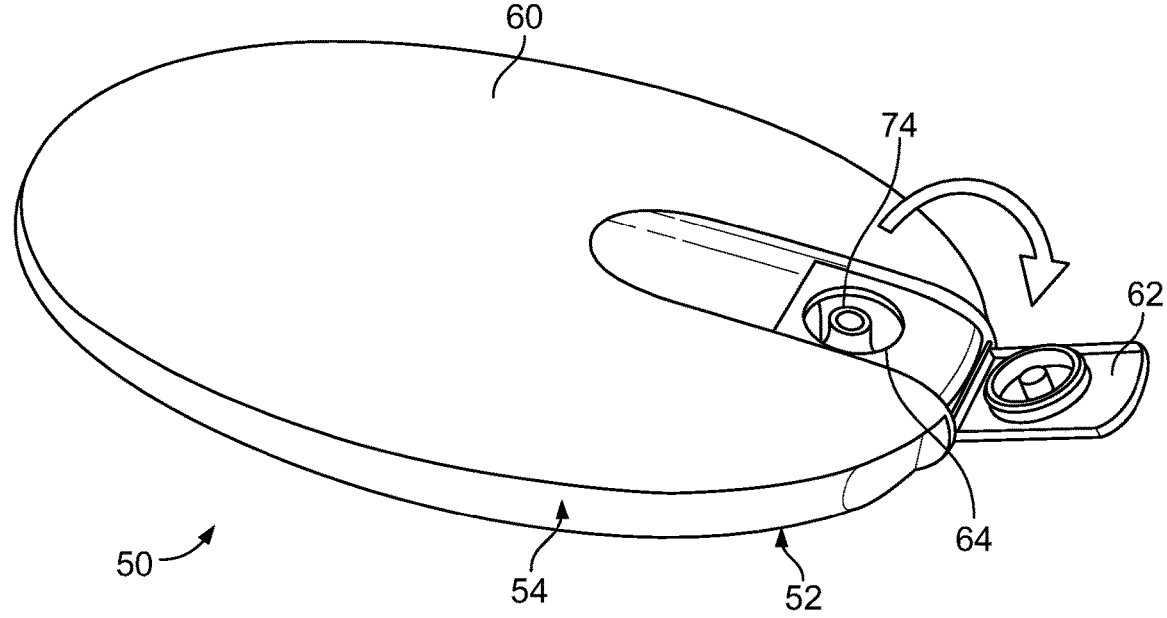
FIGS. 15 and 16 are perspective views of the kit of FIG. 14, with a cap of the housing in an open condition, and with the kit being inverted in FIG. 16.
Figures 16, 17:
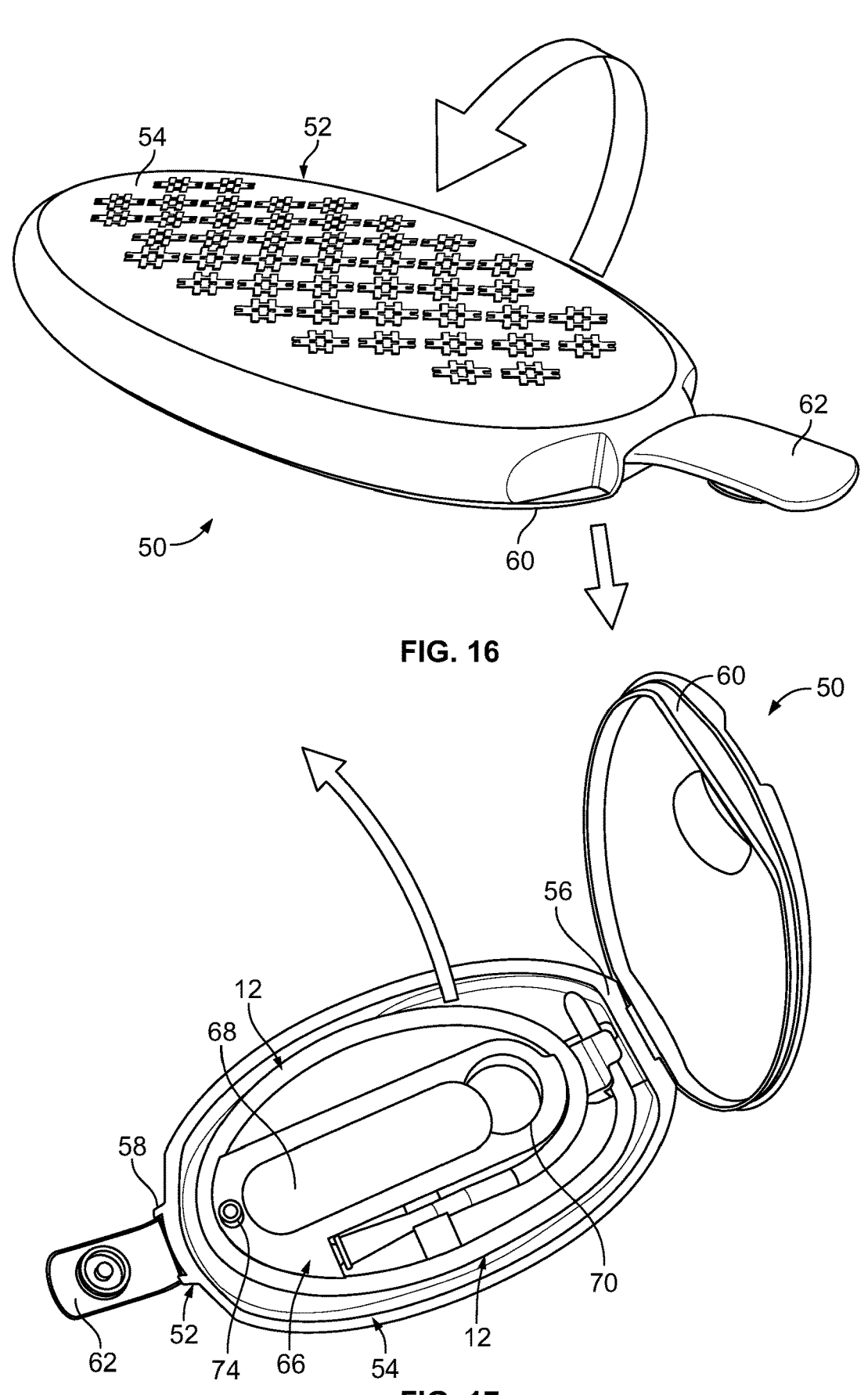
FIG. 17 is a perspective view of the kit of FIG. 14, with a lid of the housing in an open condition.

FIGS. 14-23 illustrate an alternative embodiment of a reusable urinary catheter kit 50 and a method of using and then sterilizing a reusable urinary catheter 12 of the kit 50. In the embodiment of FIGS. 14-23, the kit 50 includes a housing or body 52 having a base 54 with first and second ends 56 and 58 (FIG. 17). A lid 60 is pivotally secured to the first end 56 of the base 54, while a cap 62 is pivotally secured to the second end 58 of the base 54. The base 54, lid 60, and cap 62 may be formed of a generally rigid material, such as a plastic material.

The lid 60 and the cap 62 are each movable between a closed condition, in which they are pivoted toward the base 54 (as in FIG. 14) and an open condition in which they are pivoted away from the base 54 (as in FIG. 17). More particularly, in the closed condition, the lid 60 is positioned to contact and overlay the base 54, while the cap 62 is positioned to contact and overlay a portion of the lid 60. In the closed condition, the cap 62 overlays an aperture 64 defined in the lid 60 (FIG. 15) to provide a fluid-tight seal to a fluid flow path that is accessible via the aperture 64, as will be described in greater detail herein.

A chassis 66 is removably positioned within the housing 52 (FIG. 17). The chassis 66 may be formed of a generally rigid material, such as a plastic material, with a reusable urinary catheter 12 removably secured to the chassis 66, such as by being at least partially wrapped around the chassis 66. In the illustrated embodiment, the base 54 includes a hub 68 (FIG. 17) configured to be received within a central opening 70 defined by the chassis 66. The hub 68 serves to secure the chassis 66 within the base 54, while also properly orienting the chassis 66 within the base 54. In the illustrated embodiment, the central opening 70 is larger than the hub 68, allowing for a user to place a finger into the central opening 70 (laterally of the hub 68) to grip the chassis 66 for removal of the chassis 66 from the base 54.

The chassis 66 defines a fluid flow path 72 (FIG. 23) extending between an access opening 74 (FIG. 74) and the reusable urinary catheter 12. In the illustrated embodiment, the fluid flow path 72 extends between the access opening 74 and a funnel port 76 (FIG. 23) defined by the chassis 66. If provided, the funnel port 76 is sized and configured to be received by a distal opening 78 of a funnel 80 of the reusable urinary catheter 12, such that the fluid flow path 72 provides for fluid communication between the access opening 74 and the reusable urinary catheter 12. As shown in FIG. 15, the access opening 74 is generally aligned with the aperture 64 of the lid 60 when the chassis 66 is positioned within the base 54 and the lid 60 is in its closed condition.

The chassis 66 may be variously configured without departing from the scope of the present disclosure. In the illustrated embodiment, the chassis 66 includes a funnel clip 82, with the funnel 80 of the reusable urinary catheter 12 removably received by the funnel clip 82 (and with a distal opening 78 of the funnel 80 seated upon the funnel port 76, if provided). The illustrated chassis 66 further includes an introducer tip clip 84, with an introducer tip 86 of the reusable urinary catheter 12 received in the introducer tip clip 84. The introducer tip clip 84 may be configured to allow removal of the introducer tip 84 therefrom or may be configured for the introducer tip 86 to be retained therein during use of the reusable urinary catheter 12, as in FIG. 19.

The illustrated chassis 66 further defines an arcuate groove 88 configured to removably receive a portion of a catheter shaft 90 of the reusable urinary catheter 12. As shown in FIG. 17, the introducer tip clip 84 and the arcuate groove 88 may both be incorporated into a first extension 92 of the chassis 66, with the introducer tip clip 84 positioned outwardly of the arcuate groove 88. The chassis 66 is also shown with a perimeter groove 94, which removably receives another portion of the catheter shaft 90. In the illustrated embodiment, the funnel clip 82 and the perimeter groove 94 are both incorporated into a second extension 96 of the chassis 66, with the perimeter groove 94 positioned outwardly of the funnel clip 82.

To secure the reusable urinary catheter 12 to the illustrated chassis 66, the introducer tip 86 is pressed into the introducer tip clip 84 (if the introducer tip 86 has been removed from the introducer tip clip 84), followed by wrapping the catheter shaft 90 around the chassis 66, with portions of the catheter shaft 90 received by the perimeter groove 94 and the arcuate groove 88. The end of the chassis 66 opposite the first extension 92 may include a second perimeter groove 98, in which case a portion of the catheter shaft 90 may be received by the second perimeter groove 98 when wrapping the catheter shaft 90 around the chassis 66. Finally, the funnel 80 is pressed into the funnel clip 82 and over the funnel port 76. Alternatively, the funnel 80 may be secured to the funnel clip 82 and funnel port 76 first, followed by the catheter shaft 90 being wrapped around the chassis 66 (including being received by the arcuate groove 88, the perimeter groove 94, and the second perimeter groove 94, if provided), and then the introducer tip 86 being secured to the introducer tip clip 84. The installation process may be reversed to dissociate the reusable urinary catheter 12 from the chassis 66.

Figures 18, 19:
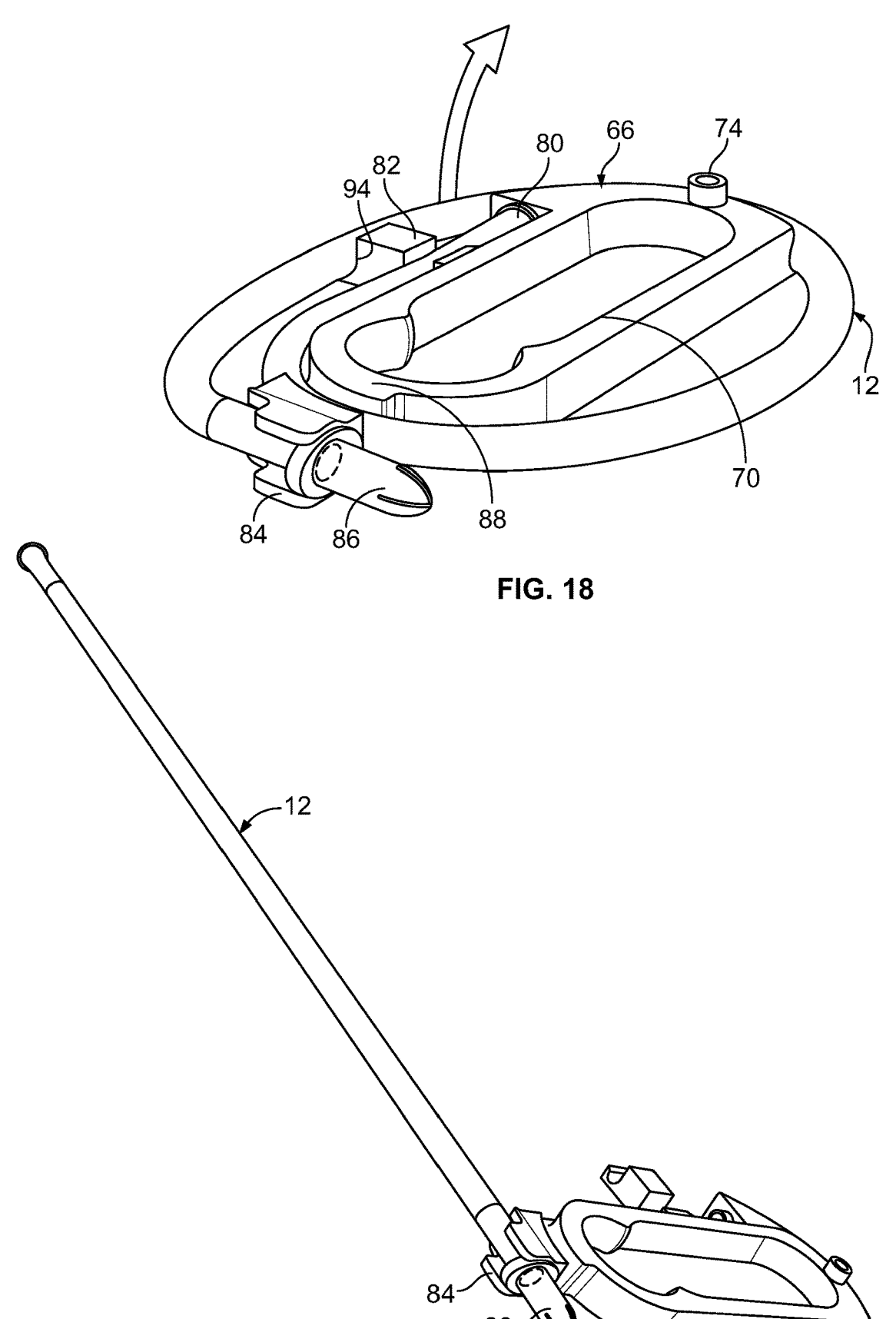
FIGS. 18 and 19 are perspective views of a chassis and reusable urinary catheter of the kit of FIG. 14.

In use, the cap 62 is rotated from its closed condition to its open condition (as in FIG. 15) to expose the aperture 64 of the lid 60 and the access opening 74 of the chassis 66. If the fluid flow channel 72 is filled with a sterilization fluid, the kit 50 is inverted to drain the sterilization fluid from the fluid flow channel 72 via the access opening 74 and the aperture 64 (FIG. 16). The kit 50 is then inverted again to orient the lid 60 to face upwardly, followed by the lid 60 being moved from its closed condition to its open condition, as in FIG. 17. Next, the chassis 66 is removed from the base 54 (FIG. 18) and the reusable urinary catheter 12 is all or partially dissociated from the chassis 66 (FIG. 19). The user then uses the reusable urinary catheter 12 for catheterization.

Figures 20, 21:
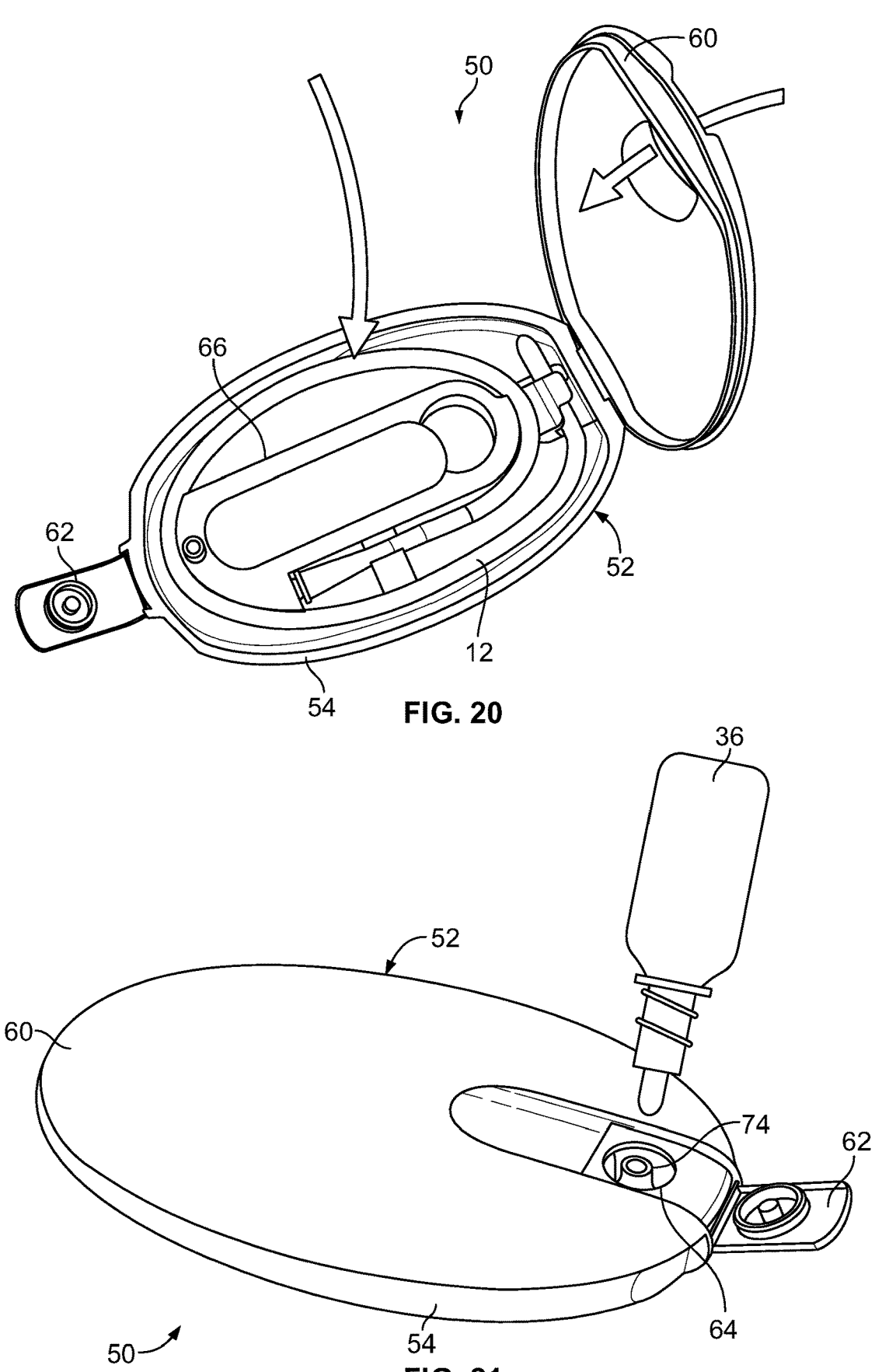
FIG. 20 is a perspective view of the kit of FIG. 14, with the lid of the housing being closed.
FIG. 21 is a perspective view of the kit of FIG. 14, with the housing being at least partially filled with a sterilization fluid.
Figure 22:
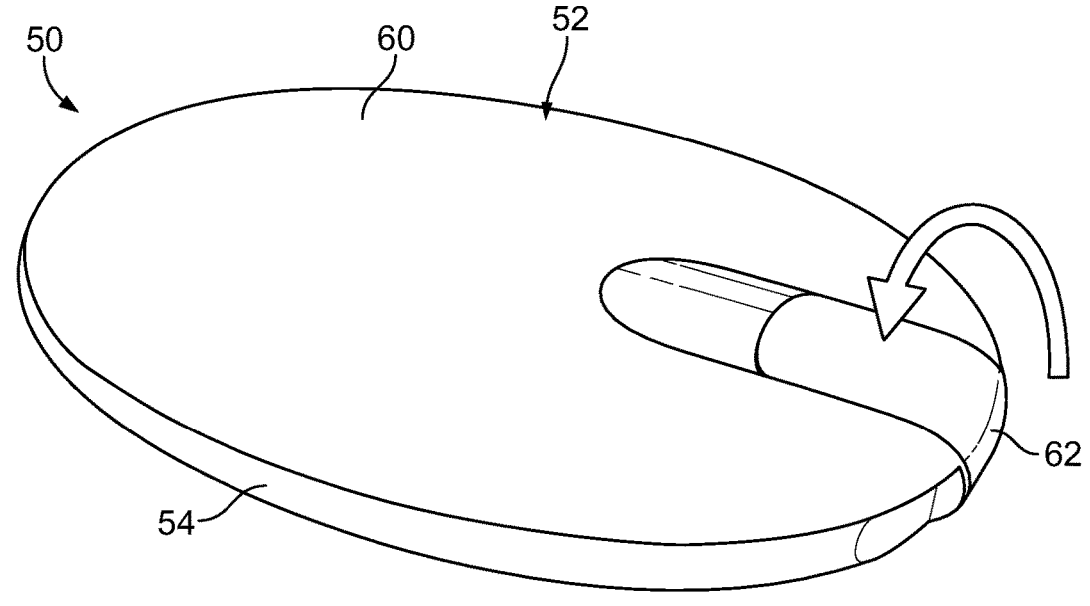
FIG. 22 is a perspective view of the kit of FIG. 14, with the lid of the housing being closed.

Following catheterization, the reusable urinary catheter 12 is reconnected to the chassis 66 and then the chassis 66 is returned to the base 54, as in FIG. 20. The lid 60 is then moved from its open condition to its closed condition, as in FIG. 21. Depending on the selected approach to sterilization of the reusable urinary catheter 12, the cap 62 may either be returned to its closed condition (as in FIG. 22) or temporarily remain in the open condition. For example, if the reusable urinary catheter 12 is to be sterilized using a sterilization fluid 36, as in FIG. 21, the cap 62 remains in its open condition to allow the fluid flow path 72 to be partially filled with the sterilization fluid 36 via the opening 64 of the lid 60 and the access opening 74. With the sterilization fluid 36 in the fluid flow path 72, the cap 62 may be returned to its closed condition (as in FIG. 22) to seal the reusable urinary catheter 12 and sterilization fluid 36 within the housing 52. The sterilization fluid 36 may be circulated through the fluid flow path 72 and along the reusable urinary catheter 12 before the next use, with the sterilization fluid 36 being emptied from the housing 52 (as in FIG. 16) prior to use.

Figure 24:
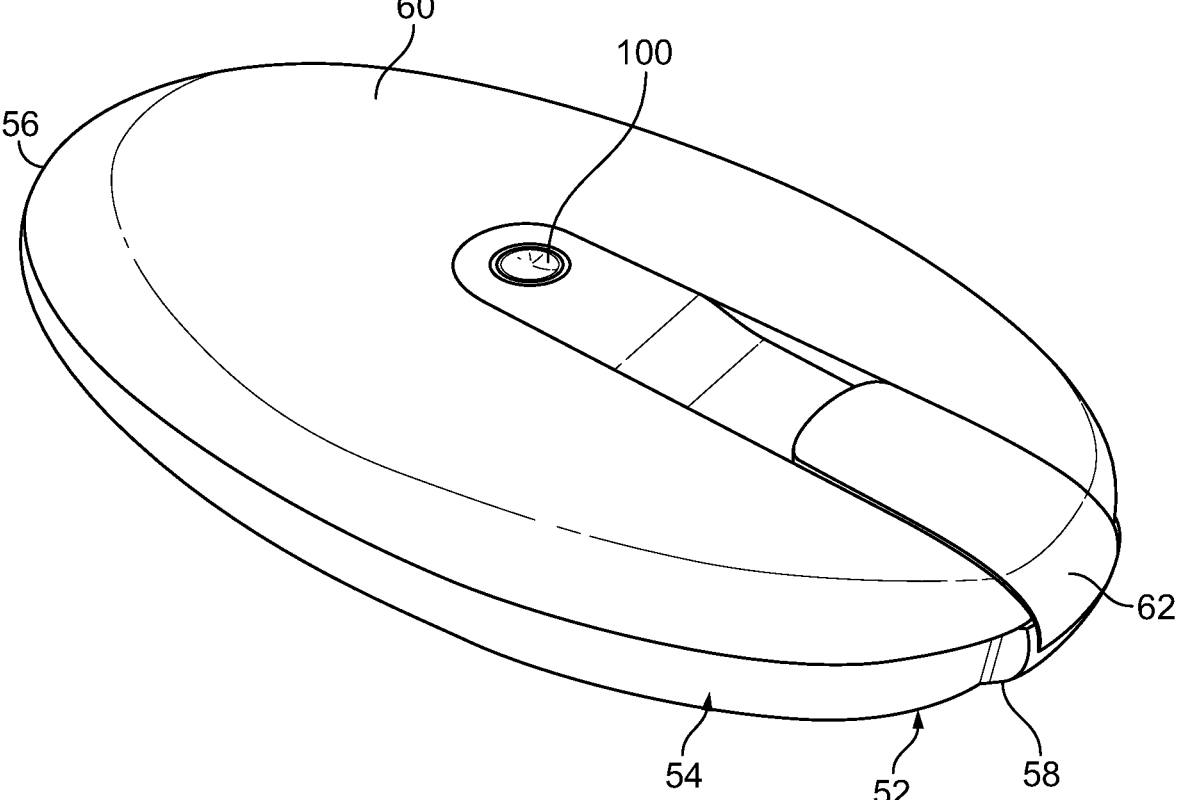
FIG. 24 is a perspective view of an alternative embodiment of the kit of FIG. 14, with a housing of the kit in a closed condition.

The manner in which the sterilization fluid 36 is circulated through the fluid flow path 72 and along the reusable urinary catheter 12 may vary without departing from the scope of the present disclosure. For example, the housing 52 may be manually agitated (e.g., by shaking it) to circulate the sterilization fluid 36 through the fluid flow path 72 and along the reusable urinary catheter 12. Alternatively, the kit 50 may be provided with a pump in fluid communication with the fluid flow path 72, which may be either manually actuated or electromechanical, as described above with respect to the embodiments of FIGS. 10-13. In yet another embodiment, at least one light source is associated with the base 54 and/or the lid 60 and configured to irradiate at least a portion of the reusable urinary catheter 12 with sterilizing light when the housing 52 is in its closed condition. If the kit 50 is provided with an electromechanical pump or a source of sterilizing light, the housing 52 may include a button or actuator 100 (FIG. 24) configured to be pressed or otherwise manipulated by a user to begin sterilization of the reusable urinary catheter 12. Such a housing 52 may also include one or more visible and/or audible indicators displaying the status of the sterilization process.

For any of the embodiments described herein that include a sterilizing light source and a hydrophilic coated catheter, the light source may be used to refresh or replenish the hydrophilic coating of the catheter. Hydrophilic catheter coatings are formed from a hydrophilic polymer. In one embodiment the sterilization fluid or hydration medium may contain a hydrophilic polymer in the fluid/medium wherein the hydrophilic polymer is the same polymer as that in the coating or one that is compatible with the hydrophilic polymer of the coating. When the sterilization fluid or hydration medium comes into contact with the hydrophilic coating of the catheter, some of the hydrophilic polymer from the fluid/medium remains on or becomes entangled with the polymer of the hydrophilic coating. Exposure to the sterilizing light source promotes or initiates cross-linking between the hydrophilic polymer of the fluid/medium and the hydrophilic coating of the catheter, thereby refreshing or replenishing the hydrophilic coating with new or additional polymer material.

It should be understood that the kits described herein are merely exemplary and that the kits may include additional components, such as a magnet configured to secure the lid of the housing in its closed condition, without departing from the scope of the present disclosure. For embodiments in which a sterilization fluid is circulated through the kit, the fluid path may include one or more filters or screens configured to entrap debris circulating through the fluid path. Each filter or screen may be placed in any suitable location within the fluid path and may be variously configured without departing from the scope of the present disclosure. In an exemplary embodiment, the filter or screen may be provided as a flat mesh with pores that are sized and configured to entrap particulates that may be present in urine. In other embodiments, the filter or screen may be differently configured (e.g., being formed of a woven or non-woven material), including having any pore size and/or porosity. If multiple filters or screens are provided, they may be substantially identical or differently configured and may be positioned at any suitable location with respect to each other. In one embodiment, the filter or screen may be placed in the return loop returning fluid to the pump for recycling. In this embodiment, the filter entraps debris prior to the fluid entering the pump and being returned back into the compartment with the catheter.

Figure 23:
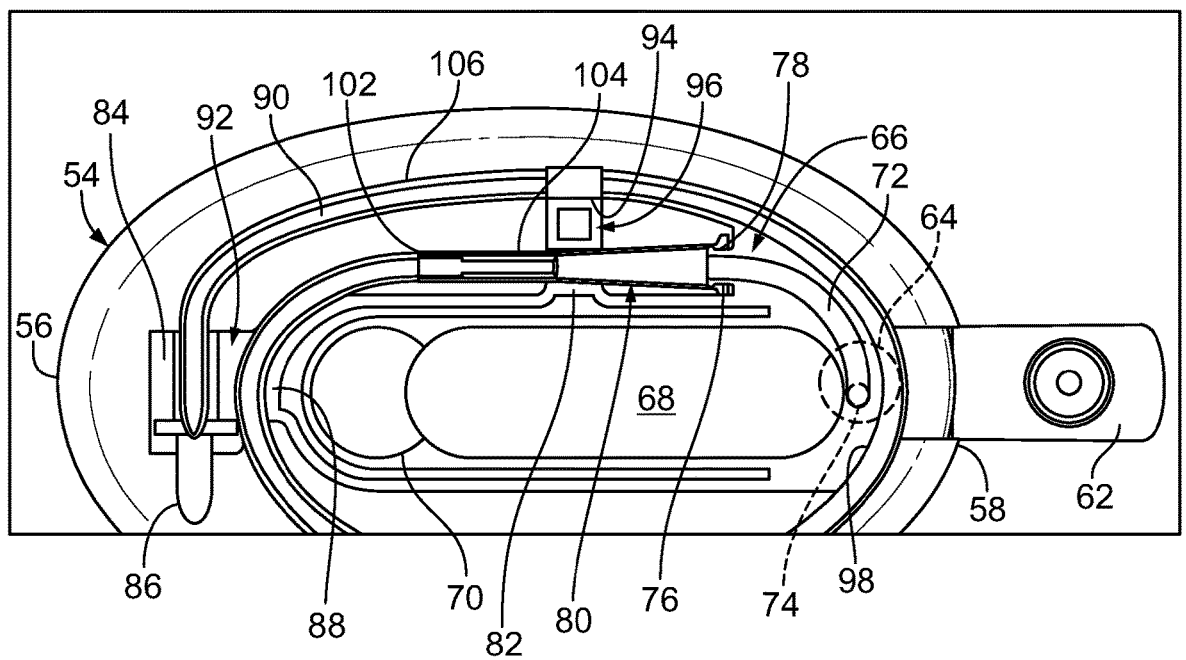
FIG. 23 is a cross-sectional view of the kit of FIG. 14.

Additionally, it is within the scope of the present disclosure for the kits and individual components thereof to be variously configured. For example, the reusable urinary catheter 12 may be provided according to conventional design or may have a different configuration. In one embodiment, the funnel 80 of the reusable urinary catheter 12 may be unconventionally configured. Such a funnel 80 may include proximal and distal openings 102 and 78 and be generally frusto-conically shaped (as is typical), but further includes a plurality of lateral apertures 104, as shown in FIG. 23. In embodiments in which a sterilization fluid is employed, it is advantageous to expose both the inner surface of the catheter shaft 90 and the outer surface of the catheter shaft 90 to the sterilization fluid. The hollow interior of the funnel 80 communicates with the hollow interior of the catheter shaft 90, so sterilization fluid conveyed into and through the funnel 80 (from its distal opening 78 to its proximal opening 102) will flow into the catheter shaft 90 to sterilize the inner surface of the catheter shaft 90. By providing a plurality of lateral openings 104, a portion of the sterilization fluid is allowed to travel from the hollow interior of the funnel 80, through the lateral openings 104, and to a position outside of the funnel 80. In the illustrated embodiment, a sleeve or sheath 106 surrounding the catheter shaft 90 extends between the introducer tip 86 and the funnel 80, with the lateral openings 104 directing sterilization fluid into the space between the sleeve 106 and the external surface of the catheter shaft 90 to sterilize the external surface of the catheter shaft 90. It should be understood that, while such a configuration may be especially advantageous for a reusable urinary catheter 12, it is also within the scope of the present disclosure for such a funnel 80 to be incorporated into a disposable urinary catheter and/or to be provided separately from a kit of the type described herein.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:
1. A reusable urinary catheter kit, comprising:
a housing including
a first member comprising a hollow,

a second member defining a lid and comprising a hollow,
a tether extending between the first and second members, the tether comprising a hollow, and
a chamber defined by the hollows of the first and second members and the tether, with the first member defining an access opening of the chamber; and
a reusable urinary catheter at least partially positioned within the chamber, wherein the second member is adjustably associated to the first member by the tether and configured to move between a closed condition in which the lid overlays the access opening to enclose the reusable urinary catheter within the chamber and an open condition in which the lid is spaced from the access opening; and wherein:
the first member includes a proximal portion and a distal portion,
the access opening is defined in the proximal portion of the first member,
the tether is connected to the distal portion of the first member,
a proximal arcuate extension is associated with and extends away from the proximal portion of the first member, and
a distal arcuate extension is associated with and extends away from the distal portion of the first member in the same direction as the proximal arcuate extension.
2. The reusable urinary catheter kit of claim 1, wherein the tether extends along a portion of the distal arcuate extension when the second member is in the closed condition.
3. The reusable urinary catheter kit of claim 1, wherein each of the proximal and distal arcuate extensions includes a free end, and the free ends of the proximal and distal arcuate extensions are positioned directly adjacent to the second member when the second member is in the closed condition.
4. The reusable urinary catheter kit of claim 3, wherein each of the free ends of the proximal and distal arcuate extensions defines an arcuate channel facing and receiving a portion of the second member when the second member is in the closed condition.
5. A reusable urinary catheter kit, comprising:
a housing including
a first member comprising a hollow, the first member including a proximal portion and a distal portion,
a second member defining a lid and comprising a hollow,
a tether extending between the first and second members, the tether comprising a hollow and the tether being connected to the distal portion of the first member,
a chamber defined by the hollows of the first and second members and the tether, with the first member defining an access opening of the chamber, the access opening being defined in the proximal portion of the first member, and
a proximal arcuate extension is associated with and extends away from the proximal portion of the first member, and
a distal arcuate extension is associated with and extends away from the distal portion of the first member in the same direction as the proximal arcuate extension; and
a reusable urinary catheter at least partially positioned within the chamber, wherein the second member is adjustably associated to the first member by the tether and configured to move between a closed condition in which the lid overlays the access opening to enclose the reusable urinary catheter within the chamber and an open condition in which the lid is spaced from the access opening, the reusable urinary being entirely removed from the chamber for use and returnable to the chamber after use.

6. The reusable urinary catheter kit of claim 5, wherein the tether extends along a portion of the distal arcuate extension when the second member is in the closed condition.

7. The reusable urinary catheter kit of claim 5, wherein each of the proximal and distal arcuate extensions includes a free end, and the free ends of the proximal and distal arcuate extensions are positioned directly adjacent to the second member when the second member is in the closed condition.

8. The reusable urinary catheter kit of claim 7, wherein each of the free ends of the proximal and distal arcuate extensions defines an arcuate channel facing and receiving a portion of the second member when the second member is in the closed condition.

9. The reusable urinary catheter kit of claim 5, wherein the housing defines a closed loop when the second member is in the closed condition.

10. The reusable urinary catheter kit of claim 5, wherein the chamber is fluid-tight when the second member is in the closed condition.

11. The reusable urinary catheter kit of claim 5, further comprising a pump in fluid communication with the chamber and configured to circulate fluid through the chamber when the second member is in the closed condition.

12. The reusable urinary catheter kit of claim 11, wherein the pump is incorporated into the second member.

13. The reusable urinary catheter kit of claim 11, wherein the pump is configured to be manually actuated.

14. The reusable urinary catheter kit of claim 11, wherein the pump is electromechanical.

15. The reusable urinary catheter kit of claim 5, further comprising at least one light source associated with the chamber and configured to irradiate at least a portion of the reusable urinary catheter with sterilizing light.

* * * * *